US005776895A

United States Patent [19]
Alber et al.

[11] Patent Number: 5,776,895
[45] Date of Patent: Jul. 7, 1998

[54] COMPOSITIONS OF G-CSF AND TNF-BP FOR PROPHYLAXIS AND TREATMENT OF SEPTIC SHOCK

[75] Inventors: Gottfried Alber, Grenzach-Whylen, Germany; Peter Angehrn, Böckten, Switzerland

[73] Assignee: Hoffman-La Roche Inc., Nutley, N.J.

[21] Appl. No.: 376,267

[22] Filed: Jan. 23, 1995

[30] Foreign Application Priority Data

Feb. 4, 1994 [EP] European Pat. Off. ............ 94810059

[51] Int. Cl.$^6$ ............ C07K 14/715; C07K 14/53; A61K 38/16; A61K 38/19
[52] U.S. Cl. ............ 514/12; 514/2; 514/885; 514/921; 424/85.1; 424/810; 424/134.1; 530/350; 530/351
[58] Field of Search ............ 424/85.1, 280.1, 424/134.1; 435/69.5; 530/351, 388.23, 387.3

[56] References Cited

U.S. PATENT DOCUMENTS

| | | | |
|---|---|---|---|
| 4,810,643 | 3/1989 | Souza | 435/69.1 |
| 4,985,241 | 1/1991 | Zimmerman et al. | 424/851 |
| 4,999,291 | 3/1991 | Souza | 435/69.1 |
| 5,073,627 | 12/1991 | Curtis et al. | 530/351 |
| 5,610,279 | 3/1997 | Brockhaus et al. | |

FOREIGN PATENT DOCUMENTS

| | | |
|---|---|---|
| 396 158 | 8/1986 | European Pat. Off. |
| 417 563 | 8/1990 | European Pat. Off. |
| WO 92/13095 | 8/1992 | WIPO |
| 93/11793 | 12/1992 | WIPO |
| 93/21946 | 4/1993 | WIPO |

OTHER PUBLICATIONS

Layton JE et al (1993) Lympholine & Cytokine Res 12(5):327.
Aderka, D. Cytokine & Growth Factor Reviews vol. 7 No. 3 pp. 231–240 1996.
Natason C. et al (1994) Annals of Internal Medicine 120(9):771–783.
Rhein, R. (1993) Biotechnology, Newswatch Oct. 3, pp. 2–3.
Stephson, J. (1996) JAMA 275(11):823–824.
Evans TJ et al (1994) J. Exp Med 180(6):2173–2179.
Satake–Ishikawa et al, Cell Struct. and Function 17:157–160 "Chem. Mod. of rG–CSF by PEG increases its biol. activity in vivo" (1992).
Ashkenazi, et al., Proceedings Of The National Academy of Sciences, vol. 88, No. 23, pp. 10535–10539 (1991).
Teng, et al., Prevention of Runting and Cachexia by a Chimeric TNF Receptor–Fc Protein, Clinical Immunology and Immunopathology, vol. 69, No. 2, pp. 215–222, (1993).
English Abstract for Document B6 Patent No. JP 04–164099 (1992).
Görgen et al., J. Immunol. 149:918–924 (1992) "Granulocyte colony–stimulating factor treatment protects rodents against ...".
Lesslauer et al., Eur. J. Immunol. 21:2883–2886 (1991) "Recombinanat soluble tumor necrosis factor receptor proteins protect mice ...".
Zanetti et al., J. Immunol. 148:1890–1897 (1992) "Cytokine production after intravenous or peritoneal gram–negative ...".
Loetscher, et al., International Congress Series Excepta Medical 2: 455–662 (1993) "Efficacy of a chimeric TNFR–IgG fusion protein ...".
Calandra, et al., Progress in Clinical and Biological Research 367: 141–159 (1991) "Anti–lipopolysaccharide and anti–tumor necrosis ...".
Niven, et al., J. of Controlled Release 32:177–189 (1994) "Pulmonary absorption of polyethylene glycolated recombinanat human ...".

*Primary Examiner*—Toni R. Scheiner
*Assistant Examiner*—John Lucas
*Attorney, Agent, or Firm*—George W. Johnston; William H. Epstein; Lewis J. Kreisler

[57] ABSTRACT

The present invention is directed to products containing G-CSF and a TNF binding protein and compositions of G-CSF and TNF-BP, and methods of treating and/or preventing septic shock by administering the products and compositions of the invention.

2 Claims, No Drawings

COMPOSITIONS OF G-CSF AND TNF-BP FOR PROPHYLAXIS AND TREATMENT OF SEPTIC SHOCK

BACKGROUND OF THE INVENTION

The present invention is directed to products containing Granulocyte Colony Stimulating Factor (G-CSF) or a pharmaceutically acceptable salt thereof and a Tumor Necrosis Factor (TNF) binding protein (TNF-BP) or a pharmaceutically acceptable salt thereof, especially in the prophylaxis and/or therapy of septic shock.

G-CSF is a fundamental factor in the differentiation and maturation of granulocytes [Metcalf, D., Blood 67, 257–267 (1986)], in particular neutrophil differentiation and proliferation. Therapy with G-CSF has been shown to result in rapid improvement of the immune status of animals with induced neutropenia [Cohen A. M. et al., Proc. Natl. Acad. Sci. USA 84, 2484–2488 (1987)] and of neutropenic patients [Gabrilove, J. L. et al., N. Engl. J. Med. 318, 1414–1422 (1988)]. Also, G-CSF diminishes the incidence of febrile episodes and nosocomially acquired infections in patients with neutropenia and cancer patients undergoing cytostatic chemotherapy [Crawford, J. et al., N. Engl. J. Med. 325, 164–170 (1991)]. G-CSF also plays an important role in the regulation of functions in mature leukocytes [Lopez, A. F. et al., J. Immunol. 131, 2983 (1983)].

Both G-CSF and soluble TNF-receptor (TNFR) fragments or chimaeric polypeptides comprising such soluble fragments reduce lethality in lipopolysaccharide (LPS)-induced septic shock in animals [Görgen, I. et al., J. Immunol. 149, 918–924 (1992); Lesslauer, W. et al., Eur. J. Immunol. 21, 2883–2886 (1991)], which is a known model for the identification of compounds useful for prophylaxis and therapy of shock in humans. In addition, models of infection-induced septic shock are even more related to the clinical situation than those of LPS-induced shock [Zanetti, G. et al., J. Immunol. 148, 1890–1897 (1992)], and G-CSF and the chimaeric polypeptide have been investigated in such a model (the shock event is elicited by generalizing *Escherichia coli* peritonitis). Whereas G-CSF and the chimaeric polypeptide alone did not show a significant increase in the survival rate, when G-CSF and the chimaeric TNF polypeptide were both applied a marked improvement in protection was seen. This synergistic result was completely unexpected.

SUMMARY OF THE INVENTION

It is an object of the present invention to provide products containing G-CSF or a pharmaceutically acceptable salt thereof and a TNF-BP or a pharmaceutically acceptable salt thereof as a combined preparation for simultaneous or sequential use in the prophylaxis and/or therapy of septic shock.

This invention is also directed to a composition containing G-CSF or a pharmaceutically acceptable salt thereof and a TNF binding protein or a pharmaceutically acceptable salt thereof and a pharmaceutically acceptable carrier.

In this composition, the TNF binding protein may be or may contain the TNF receptor, or a part of the TNF receptor which binds TNF. In particular, the TNF binding protein may be or may contain a part of the p55- or p75-TNF-receptor which binds TNF, especially a soluble part of the p55- or the p75-TNF-receptor which soluble part binds TNF. A preferred TNF binding protein is a chimaeric polypeptide which comprises a soluble part of the p55- or the p75-TNF-receptor and all or parts of the constant domains of the heavy or light chain of human immunoglobulin. In a particularly preferred protein, the immunoglobulin component is all domains except the first domain of the constant region of the heavy chain of human immunoglobulin IgG, IgA, IgM or IgE, especially an IgG such as IgG1 or IgG3. The TNF binding protein may also be or contain an antibody to TNF.

In this composition, the G-CSF is natural G-CSF, or recombinant G-CSF expressed in a prokaryotic or heterologous eukaryotic cell, especially in a in a prokaryotic cell. In any event, the G-CSF may be a modified protein, for example the G-CSF may be modified by the attachment of a PEG molecule.

This invention is also directed to a kit containing separate components for prevention (prophylaxis) or treatment of septic shock, which are G-CSF or a pharmaceutically acceptable salt thereof and TNF binding protein or a pharmaceutically acceptable salt thereof, in particular a kit wherein each component is provided in such an amount as to act in synergy with the other component. Any TNF binding protein or G-CSF mentioned in this application may be used as a component in this kit. In particular, the TNF binding protein may be a chimaeric polypeptide which comprises a soluble part of the p55 or p75 TNF receptor and parts of the constant domains of the heavy chain of human immunoglobulin, which parts comprise all domains except the first domain of the constant region of the heavy chain of human immunoglobulin IgG1 or IgG3.

This invention additionally covers methods of preventing or treating septic shock by administering to a patient (for example a patient in danger of septic shock or after onset of septic shock) a composition of this invention in an amount effective to prevent or to treat septic shock. Also, part of this invention is a method of treating or preventing septic shock which method comprises administering to a patient in separate and simultaneous doses an amount of G-CSF and an amount of TNF binding protein effective in combination to treat or prevent septic shock, as is a method of treating or preventing septic shock which method comprises administering to a patient in separate and successive doses an amount of G-CSF and an amount of TNF binding protein which in combination treat or prevent septic shock. In the successive dosing regimen, either component may be administered first.

DETAILED DESCRIPTION OF THE INVENTION

The term G-CSF in the context of the present specification and claims is used in its broadest sense in view of a protein having the biological activity of G-CSF as understood by the skilled artisan and comprises polypeptides (either of natural or synthetic including recombinant origin, either modified or not) as defined and described (including their preparation and use) in the scientific literature and, e.g., in any of the following patent publications: DE 30 27 105, EP 169 566, EP 215 126, EP 237 545, EP 396 158, EP 220 520, EP 217 404, EP 230 980, EP 231 819, DE 37 23 781, EP 263 490, EP 344 796, EP 355 811, EP 373 679, EP 401 384, EP 456 812, EP 459 630, EP 459 516, EP 459 795, EP 243 153, EP 272 703, EP 331 186, EP 335 423, WO 93/15211. A preferred G-CSF is disclosed in EP 237 545 [human pluripotent G-CSF (hpG-CSF)], which is a recombinant molecule, optionally containing a methionine residue at its N-terminus. Most particularly preferred is a G-CSF having the specific amino acid sequence provided in EP 237 545 and encoded by DNA sequences also provided in EP 237 545.

The term G-CSF comprises, in addition to G-CSF of natural origin, any G-CSF coded by a DNA sequence which upon expression by conventional methods in a prokaryotic or eukaryotic (and preferably heterologous) host cell yields a polypeptide product having at least a part of the primary structure, and one or more of the biological properties of naturally-occurring hpG-CSF, which structure and properties are as defined in EP 237 545. Prokaryotic expression may be accomplished using known prokaryotic vectors and hosts, and may yield a G-CSF of this invention which has the characteristics of a prokaryotic expression product (for example an unglycosylated G-CSF). The DNA sequence may be selected from among:

(a) the DNA sequence set out in Table VII of EP 237 545 or complementary strands;

(b) DNA sequences which hybridize to the DNA sequence of Table VII of EP 237 545 under any suitable hybridization conditions, e.g., as illustrated in EP 237 545 or described in "Molecular Cloning", Sambrook et al. 1989, Cold Spring Harbor Laboratory Press, Cold Spring Harbor; and (c) DNA sequences which, but for the degeneracy of the genetic code, would hybridize to the DNA sequences defined in (a) or (b) which sequences code for a polypeptide having the same amino acid sequences as those provided in EP 237 545.

DNA sequences which hybridise with those sequences defined above, herein termed mutant DNA sequences, can be prepared by random or site directed mutagenesis or by chemical synthesis or by polymerase chain reaction (PCR) -technology using primers defined on the basis of the DNA sequences given in EP 237 545 by methods known in the art and described, e.g., by Sambrook et al. (s.a.) or for the PCR technology by Innis et al. [PCR Protocols: A Guide to Methods and Applications, Academic Press, Inc. (1990)]. Thus using such mutant DNA sequences, mutant G-CSFs which are comprised by the term "G-CSF" can be prepared by methods known in the art and described, e.g., in the above mentioned patent publications. Mutant G-CSFs are defined and their preparation described especially in EP 243 153, WO 90/12874, WO 89/05824, EP 272 703 and EP 456 200.

As stated above the term G-CSF comprises G-CSF, either of natural or recombinant origin, also in modified form, e.g., coupled to chemical entities which without altering the basic biological activity of G-CSF are capable of modifying it in a therapeutically advantageous way, for example by improving its stability or solubility, or reducing its immunogenicity. A preferred and well known modification of polypeptides such as G-CSF is by coupling to water soluble polymers, such as polyethylene glycols or polypropylene glycols, within a wide range of molecular weights, e.g., from 500 to 20,000 daltons. This coupling provides protected G-CSFs, e.g., pegylated G-CSF, which should be substantially non-immunogenic. Various methods of coupling the polymer with G-CSF via different known linkers are known in the art and available to a skilled person. For example, some are described in general in "Perspectives in Bioconjugate Chemistry", ed. C. F. Meares, American Chemical Society, Washington 1993, and specifically in U.S. Pat. No. 4,179, 337. Modified G-CSFs and their preparation are described in EP 401 384, EP 335 423 and EP 473 268. Modified G-CSF also comprises G-CSF which shows a different glycosylation pattern than that known for naturally occurring or recombinant G-CSF, in particular by the addition of at least one polycarbohydrate chain as described in EP 370 205.

The term TNF binding protein (TNF-BP) includes any protein or fragment of a protein being composed of sufficient amino acids to form a structure to which human TNF can bind, irrespective of where or how the protein is obtained. Binding to TNF may be determined by conventional binding or binding competition assays using human TNF, for example as described in EP 417 563. TNF-BP can be an antibody to TNF (such as a monoclonal antibody obtained for example by conventional hybridoma technology using TNF as an immunogen) but also any type of chimaeric antibody to human TNF as described, e.g., in WO 91/02078. Such a chimaeric antibody is an antibody in which different parts of the molecule originate from different sources, specifically from human and from animal (such as mouse, rat or rabbit) sources. In a preferred embodiment of such antibodies only the complementary determining regions are of non-human origin, and if desired additional amino acids in the variable regions. These antibodies can be prepared according to methods known in the art and as described, in EP 239 400 or in WO 90/07861.

A TNT-BP as defined above can also be any naturally occurring or recombinantly made TNF-receptor (TNFR) or part thereof, preferably a protein which comprises a part of or is derived from a part of the human p55- or p75-TNFR, which part still binds TNF, such as a soluble part of these receptors. A TNFR can also be a chimaeric polypeptide which comprises a soluble part of the p55 or p75 TNFR and all or parts of at least one constant domain of the heavy or the light chain of a human immunoglobulin. Preferred are such chimaeric polypeptides wherein the TNF binding part is all or a part of or derived from the human p55-TNFR. Furthermore such chimaeric polypeptides are preferred wherein the immunoglobulin part comprises all domains except the first domain of the constant region of the heavy chain of a human immunoglobulin such as IgG, IgA, IgM or IgE, especially IgG, in particular IgG1 or IgG3.

Any amino acid of the immunoglobulin part or the TNF binding part of the chimaeric polypeptide can be deleted, or substituted by one or more amino acids, or one or more amino acids can be added, as long as the TNF binding part still binds TNF and the immunoglobulin parts retains one or more of its well-known characteristic properties. The same is true for a TNF-BP as defined above that is not part of a chimaeric polypeptide with an immunoglobulin.

TNF-BPs, their isolation from natural sources or their preparation by recombinant methods, including the preparation of specific constructs such as chimaeric polypeptides comprising in addition to the TNF binding part an immunoglobulin part, are described in the following patent publications: EP 308 378, EP 422 339, GB 2 218 101, EP 393 438, WO 90/13575, EP 398 327, EP 412 486, WO 91/03553, EP 418 014, JP 127,800/1991, EP 433 900, U.S. Pat. No. 5,136,021, GB 2 246 569, EP 464 533, WO 92/01002, WO 92/13095, WO 92/16221, EP 512 528, EP 526 905, WO 93/07863, EP 568 928, WO 93/21946, WO 93/19777 and EP 417 563 and by Loetscher et al. (J. Biol. Chem. 266, 18324–18329, 1991; in case of the purification of a chimaeric polypeptide comprising a part of IgG1 the protein G affinity purification step is replaced by a protein A affinity purification step with which a man skilled in the art is familiar with). Specifically preferred are TNF-BPs in the form of recombinant soluble parts of the human TNFR, especially the p55-TNFR, which parts binds TNF, or chimaeric polypeptides comprising such soluble parts and immunoglobulin parts as defined above and as described in EP 417 563. The definition of TNF-BP of the present invention includes TNF-BPs which have been modified chemically by means known in the art and as described above for G-CSF, e.g., by linkage to a water soluble polymer, e.g., polyethyleneglycol or polypropyleneglycol by methods described in the state of the art, e.g., in WO 92/16221.

Furthermore it is an object of the present invention to provide products or compositions as defined above wherein either the G-CSF or the TNF-BP or both are in the form of a pharmaceutically acceptable salt. As used herein the term "pharmaceutically acceptable salt" refers to both salts of the products of the present invention, i.e. TNF-BP or G-CSF. Such salts are salts of a carboxyl group and may be formed by means known in the art and include inorganic salts, for example, sodium, calcium, ammonium, ferric or zinc salts, and the like, and salts with organic bases as those formed with amines, such as triethanolamine, arginine or lysine, piperdine, procaine and the like. Acid addition salts include salts with mineral acids such as hydrochloric acid or sulfuric acid, and salts with organic acic or sulfuric acid, and salts with organic acids such as acetic acid or oxalic acid.

Further objects of the present invention are the use of G-CSF or a pharmaceutically acceptable salt thereof in the manufacture of a medicament, especially for the prophylaxis and/or treatment of septic shock in patients also receiving a TNF-BP or a pharmaceutically acceptable salt thereof as defined above, and also the use of a TNF binding protein or a pharmaceutically acceptable salt thereof as defined above in the manufacture of a medicament, especially for the treatment and/or prophylaxis of septic shock in patients also receiving G-CSF or a pharmaceutically acceptable salt thereof.

Products containing G-CSF and TNF-BP may be in the form of a combination, or kit, preferably in the form of a "kit-of-parts" arrangement containing the active ingredients in separate compartments intended for separate and simultaneous or successive administration, especially in the prophylaxis and/or therapy of septic shock.

A preferred kit contains G-CSF or a pharmaceutically acceptable salt thereof and TNF-BP or a pharmaceutically acceptable salt thereof as separate components. Each component is provided so as to act synergistically with the other component. Synergistic dosages are obtained by determining an appropriate dosage as described below, then determining the range of proportions of components within the preferred dosages which provide superior results in alleviated septic shock compared to either component alone The assay provided in the Example may be used for this purpose, or any known assays for determining activity against septic shock.

Any of the TNF-BPs and G-CSFs described herein may be used as components of a kit. A preferred TNF-BP is a chimaeric polypeptide as described which comprises a soluble part of the p55 or p75 human TNF receptor and all domains except the first domain of the constant region of the heavy chain of an immunoglobulin IgG, IgA, IgM or IgE, especially an IgG such as IgG1 or IgG3.

Accordingly G-CSF and TNF-BP are administered to a patient separately and simultaneously (at the same time) or separately and successively (one after the other). When so administered, the TNF-BP and G-CSF act synergistically against septic shock. The combination or kit may also contain G-CSF and TNF-BP in the form of a mixture in the same compartment Methods of preventing or treating septic shock by administering both a TNF-BP or a pharmaceutically active salt thereof and G-CSF or a pharmaceutically active salt thereof or a composition containing both are objects of the present invention. The method may involve preventing septic shock by administering to a patient at risk for septic shock a TNF-BP and G-CSF composition of this invention in an amount effective to prevent septic shock, or by administering to a patient in separate and simultaneous or separate and successive doses an amount of G-CSF and an amount of TNF binding protein effective in combination to prevent septic shock.

Methods of this invention include methods of treating septic shock by administering to a patient after the onset of septic shock a TNF-BP and G-CSF composition of this invention in an amount effective to treat septic shock, or administering in separate and simultaneous or separate and successive doses an amount of G-CSF and an amount of TNF binding protein effective in combination to treat septic shock.

Suitable dosage levels for TNF-BP and G-CSF for a given patient for prophylaxis or for treatment may be determined by a skilled person based on the information provided below. These dosage levels may be used for administering TNF-BP and G-CSF together but in separate doses, or together in the form of a composition. Synergism between TNF-BP and G-CSF is expected in either regimen.

TNF-BP may be administered so as to create a preselected concentration range of TNF-BP in the patient's blood stream. Maintenance of circulating concentrations of TNF-BP of more than 0.01 ng per ml of plasma is preferred. A useful dosage range for the treatment of septic shock is between about 0.1–200 mg per kg of patient body weight per 24 hours administered in equal doses between about 4–15 times per 24 hours. The frequency of dosing and the optimal dose will depend on pharmacokinetic parameters of the TNF-BP in the formulation used.

The dosage level and administration frequency of G-CSF may be appropriately determined by one skilled in the art based on factors such as the severity of the shock state to be treated, body weight, age and sex of the patient, and the route of administration. Typically a dosage containing about 10–2000 µg/kg, preferably about 50–1500 µg/kg, most preferably about 10–250 µg G-CSF/kg body weight may be administered.

Administration of compositions of this invention or use of a kit of this invention for treatment of septic shock should begin, under any mode of treatment, as soon as possible after the onset of septic shock, i.e. when septicemia has occurred and is diagnosed. Prophylactic administration may begin immediately following surgery or an accident or any other event that may include a risk of septic shock.

Regardless of the manner of administration, the specific dose is calculated by known methods according to the approximate body weight of the patient. Further refinement of the calculations necessary to determine appropriate dosage for treatment involving each of the above mentioned formulations may be routinely made by one skilled in the art.

A composition of G-CSF and TNF-BP may be administered, formulated, prepared, handled, and stored by the same methods described for the individual components G-CSF or TNF-BP. Thus the following applies to G-CSF and TNF-BP as separate components of a kit, and also together in the form of a composition.

In the prophylaxis (prevention) and/or treatment of septic shock by the above mentioned method, G-CSF may be administered to a patient by any route known in the state of the art, e.g., intramuscularly, intravenously, subcutaneously (e.g. by a subcutaneous implant as described in EP 246 322), orally in the form of a specific oral dosage form as described for example in EP 459 516 and EP 459 795, pernasally as described for example in EP 565 722 or by pulmonary administration as described for example in EP 505 123.

G-CSF may be formulated in a suitable dosage form according to the specific route of administration selected. When G-CSF is obtained as a G-CSF solution or composition by any of the known methods described or referred to herein, it is preferentially kept in solution at about 4° C. but, depending on the type of G-CSF obtained, may also be stored in a frozen state. Alternatively, the solution may be stored in lyophilized form after being dehydrated by freeze-drying or vacuum drying (as described, e.g., for PEG-G-CSF in EP 335 423). If desired, the G-CSF may be kept in an appropriate conventional buffer, and processed before use by aseptic filtration through a millipore filter or any other suitable conventional means so as to formulate an injectable preparation.

In order to formulate a dosage form that is suitable for administration to the patient through a given route, the G-CSF to be used in the method of treatment of the present invention may contain appropriate additives selected from known pharmaceutical carriers, excipients, diluents, stabilizers (such as proteins, for example human serum albumin), anti-adsorption agents, preservatives, solubilizers and emulsifiers as described, e.g., in DE 37 23 781 or may be in the form of a stabilized hydrophobic formulation as described e.g. in EP 373 679 or in the form of a sustained release particulate preparation as described, e.g., in EP 263 490 or EP 58 481 or for pegylated G-CSF as described, e.g., in EP 473 268.

The TNF-BP of the present invention is preferably administered parenterally by injection, although other effective administration forms, such as intraarticular injection, orally active formulations, transdermal iontophoresis or suppositories, are also possible. One preferred carrier is physiological saline solution, but it is contemplated that other pharmaceutically acceptable carriers may also be used. The primary solvent in such a carrier may be either aqueous or non-aqueous in nature. In addition, the carrier may contain other pharmacologically acceptable excipients known for modifying or maintaining the pH, osmolarity, viscosity, clarity, color, sterility, stability, rate of dissolution, or odor of the formulation. Similarly, the carrier may contain still other pharmacologically acceptable excipients for modifying or maintaining the stability, rate of dissolution, release, or absorption of the TNF-BP. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or a form requiring reconstitution immediately prior to administration. The preferred storage temperature for such formulations is at least as low as 4° C. and preferably at −70° C. It is also preferred that such formulations containing TNF-BPs are stored and administered at or near physiological pH.

EXAMPLE

Septic Shock Induced by Generalized *E. coli* Peritonitis

Swiss albino mice (Jbm MoRo, weight 16 to 20 g) were injected with aqueous solution of G-CSF (Neupogen, Hoffmann-La Roche, Basle, CH; 0.1 mg/kg sc) and/or TNFR/IgG3 (a TNF-BP as described in EP 417 563 consisting of the first 182 amino acids of the human p55-TNFR fused to the hinge region of human IgG3 heavy chain and expressed in mouse J558L myeloma cells; 2.5 mg/kg ip) as designated in Table 1. Peritonitis was induced by intraperitoneal injection of $10^6$ CFUs (colony-forming units) of an overnight culture of *E. coli* 25922, which is about 500 times the number of organisms required to kill 50% of unmedicated animals within 72 hours. Control and treatment groups were composed of 5–10 mice each. The developing generalized infection was stopped in all animals by the administration of ceftriaxone (Hoffmann-La Roche, Basle, CH; 1 mg/kg sc) 3.8 hours after bacterial challenge. This resulted in bacterial clearance of the bloodstream, but was too late to prevent lethal septic shock in >80% of unprotected animals. Surviving mice received an additional ceftriaxone treatment 24 hours after challenge. The rate of survival was read 24, 48 and 72 hours after infection. Animals that were severely sick and unable to eat and drink 21 hours or later after challenge were sacrificed and registered as therapeutic failures. For control heart blood was taken from at least one dead or sacrificed mouse in the treatment groups and the control group and cultivated on agar. The summarized data of several experiments performed with G-CSF and the specific TNF-BP mentioned are presented in Table 1. When given as single compounds, G-CSF yielded a 20% rate of survival and the specific TNF-BP a 22% survival rate. These differences to the saline control group with 10% rate of survival are not significant. A marked improvement in protection was achieved by combining G-CSF and the specific TNF-BP. All mice survived when G-CSF was given thrice, i.e. 48 h, 24 h, and 2 h before infection, in the combination regimen. All these animals showed visible signs of beginning septic shock 3 hours after infection as did the control animals. However, they did not die and began to recover about 24 hours after challenge. When the last dose of G-CSF 2 h before infection was omitted in the combined regimen, the rate of protection decreased to 65%. The viable bacterial count 3.8 h after challenge when the septicemia was stopped by the administration of ceftriaxone, was only slightly lower in the G-CSF plus the specific TNF-BP group than in the saline group ($2.6 \times 10^8$ CFU/ml vs. $3.5 \times 10^8$ CFU/ml, respectively). The endotoxin content of G-CSF (25 µg/ml) and TNFR/IgG3 (250 µg/ml) has been determined in a limulus amebocyte lysate assay (sensititvity: 0.06 EU/ml) as known in the art to be <0.05 EU/ml. Accordingly desensitization against LPS can be excluded. Dose dependency of G-CSF in *E. coli*-induced shock in Swiss albino mice is shown in Table 2 (G-CSF was administered in varying doses as indicated 48 hs, 24 hs and 2 hs before challenge and 50 µg TNFR/IgG3/mouse were administered 2 hs before challenge).

TABLE 1

| Compound(s) | Regimen* | Animals used | Animals surviving after 72 hs | Survival (%) |
|---|---|---|---|---|
| G-CSF | A | 10 | 2 | 20** |
| TNFR/IgG3 | C | 45 | 11 | 22** |
| G-CSF + TNFR/IgG3 | A + C | 10 | 10 | 100** |
| G-CSF + TNFR/IgG3 | B + C | 20 | 13 | 65** |
| Saline | D | 20 | 2 | 10** |

*Regimen:
A, G-CSF (0.1 mg/kg sc) was administered 48 h, 24 h, and 2 h before challenge
B, G-CSF (0.1 mg/kg sc) was administered 48 ha and 24 h before challenge
C, TNFR/IgG3 (2.5 mg/kg ip) was administered 2 h before challenge
D, physiological saline was administered ip 48 h, 24 h and 2 h before challenge
**Significances [Fisher's Exact Test, 2-Tail Procd. FREQ. SAS 6.08 Inst. Carry N.C.)]:

TABLE 1-continued

| Compound(s) | Regimen* | Animals used | Animals surviving after 72 hs | Survival (%) |
|---|---|---|---|---|
| G-CSF + TNFR/IgG3 (regimen A + C) to saline control, p < 0.005 | | | | |
| G-CSF + TNFR/IgG3 (regimen A + C) to G-CSF, p < 0.005 | | | | |
| G-CSF + TNFR/IgG3 (regimen A + C) to TNFR/IgG3, p < 0.005 | | | | |
| G-CSF + TNFR/IgG3 (regimen B + C) to saline control, p < 0.005 | | | | |
| G-CSF + TNFR/IgG3 (regimen B + C) to G-CSF, p = 0.05 | | | | |
| G-CSF + TNFR/IgG3 (regimen B + C) to TNFR/IgG3, p < 0.005 | | | | |

TABLE II

| Pretreatment | Challenge E. coli [ATCC 25922] | Survivors/ total |
|---|---|---|
| Saline | + | 1/10 |
| G-CSF (5.00 µg) + TNFR/IgG3 | + | 8/10 |
| G-CSF (1.00 µg) + TNFR/IgG3 | + | 7/10 |
| G-CSF (0.20 µg) + TNFR/IgG3 | + | 7/10 |
| G-CSF (0.04 µg) + TNFR/IgG3 | + | 3/10 |

We claim:

1. A composition which contains G-CSF or a pharmaceutically acceptable salt thereof and a TNF binding protein which is a chimaeric polypeptide which comprises the soluble part of the p55 TNF receptor and all domains except the first domain of the constant region of the heavy chain of human immunoglobulin IgG1 or IgG3 or a pharmaceutically salt thereof, in a combined amount effective to prevent or treat septic shock, and a pharmaceutically acceptable carrier.

2. A composition in accordance with claim 1, wherein the human immunoglobulin is IgG3.

* * * * *